(12) United States Patent
Bjork et al.

(10) Patent No.: US 12,740,869 B2
(45) Date of Patent: Sep. 22, 2026

(54) FIXATED INTERVERTEBRAL MESH IMPLANT AND METHOD

(71) Applicant: Spineology Inc., St. Paul, MN (US)

(72) Inventors: Todd Bjork, Hudson, WI (US); Michael Wang, Miami, FL (US)

(73) Assignee: Spineology Inc., St. Paul, MN (US)

( * ) Notice: Subject to any disclaimer, the term of this patent is extended or adjusted under 35 U.S.C. 154(b) by 513 days.

(21) Appl. No.: 17/881,573

(22) Filed: Aug. 4, 2022

(65) Prior Publication Data

US 2023/0041167 A1 Feb. 9, 2023

Related U.S. Application Data

(60) Provisional application No. 63/229,415, filed on Aug. 4, 2021.

(51) Int. Cl.
*A61F 2/44* (2006.01)
*A61F 2/30* (2006.01)

(52) U.S. Cl.
CPC ........ *A61F 2/4455* (2013.01); *A61F 2/30771* (2013.01); *A61F 2002/30785* (2013.01); *A61F 2002/30841* (2013.01)

(58) Field of Classification Search
CPC ........ A61F 2/4455; A61F 2/441; A61F 2/442; A61F 2002/444; A61F 2002/4435
See application file for complete search history.

(56) References Cited

U.S. PATENT DOCUMENTS 7,273,497 B2 * 9/2007 Ferree .................. A61F 2/4611 623/17.16
8,906,094 B2 * 12/2014 Roche ................ A61B 17/7097 623/17.12
9,844,444 B2 12/2017 Wolfe
10,874,524 B2 12/2020 Bjork
11,439,515 B2 9/2022 Gleason
12,226,323 B2 * 2/2025 Wolff .................... A61F 2/4611
2001/0010002 A1 * 7/2001 Michelson ........... A61B 17/025 606/57
2007/0270876 A1 * 11/2007 Kuo .................. A61B 17/7098 606/92
2009/0234457 A1 * 9/2009 Lotz ........................ A61L 27/52 623/1.15
2016/0015521 A1 * 1/2016 Serrahima Tornel ... A61F 2/442 623/17.16
2019/0314167 A1 * 10/2019 Bender ............... A61F 2/30749
2019/0336305 A1 * 11/2019 Joly .................... A61F 2/30734
2020/0129305 A1 * 4/2020 Sansur .................. A61F 2/4455

* cited by examiner

*Primary Examiner* — Ellen C Hammond

(57) ABSTRACT

A mesh implant and/or container may be used as an intervertebral implant. The mesh implant may be anchored or otherwise fixed to the vertebral endplates to prevent the implant from migrating forward and out anteriorly to the spinal column. The mesh implant may be knitted with a rip stop, elastic or other stich pattern to prevent unraveling or tearing.

14 Claims, 4 Drawing Sheets

FIXATED INTERVERTEBRAL MESH IMPLANT AND METHOD

PRIORITY

This application claims the benefit of U.S. Provisional Application Ser. No. 63/229,415, filed on Aug. 4, 2021, which is hereby incorporated herein by reference in its entirety.

FIELD

The present invention generally relates to surgical techniques, devices, tools and systems, and more particularly to techniques, devices, tools and systems for spinal surgery.

BACKGROUND

Advancements in spine surgery have led to many procedures being performed using minimally invasive techniques. Such minimally invasive techniques may reduce risk, injury and trauma to surrounding anatomy, reduce blood loss and reduce surgical time. There remains a need for additional minimally invasive spinal deformity correction procedures, tools and devices.

SUMMARY

The present invention in certain embodiments includes a technique wherein the Anterior Longitudinal Ligament ("ALL") is sectioned. The ALL may be sectioned under fluoroscopic or endoscopic control. In an example preferred embodiment, direct visualization using an endoscope is employed. Any interbody distraction thereafter will likely lead to substantial lordosis, up to 30 degrees per disc level. Constraints on the degree of lordosis may include: the amount of ALL sectioned, facet joint stiffness, and the ability of the interbody implant and vertebral endplates to deliver a distracting force.

In a preferred embodiment, a mesh implant and/or container, such as for example as is disclosed in U.S. Pat. No. 8,906,094 may be used as the intervertebral implant. U.S. Pat. No. 8,906,094 is hereby incorporated by reference herein in its entirety. In such an embodiment, the mesh implant may be anchored or otherwise fixed to the vertebral endplates to prevent the implant from migrating forward and out anteriorly to the spinal column. The mesh implant may be knitted with a rip stop, elastic or other stich pattern to prevent unraveling or tearing.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
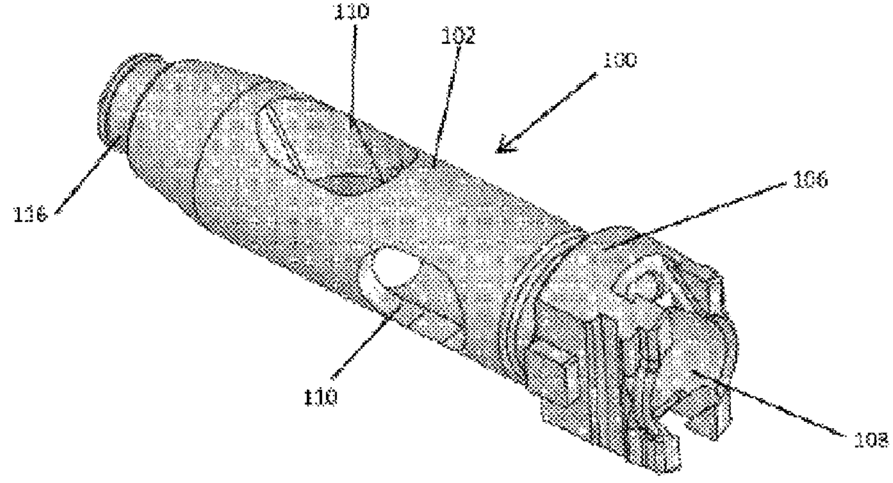
FIG. 1 is a perspective view of an implant anchor in accordance with certain embodiments of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Figure 2:
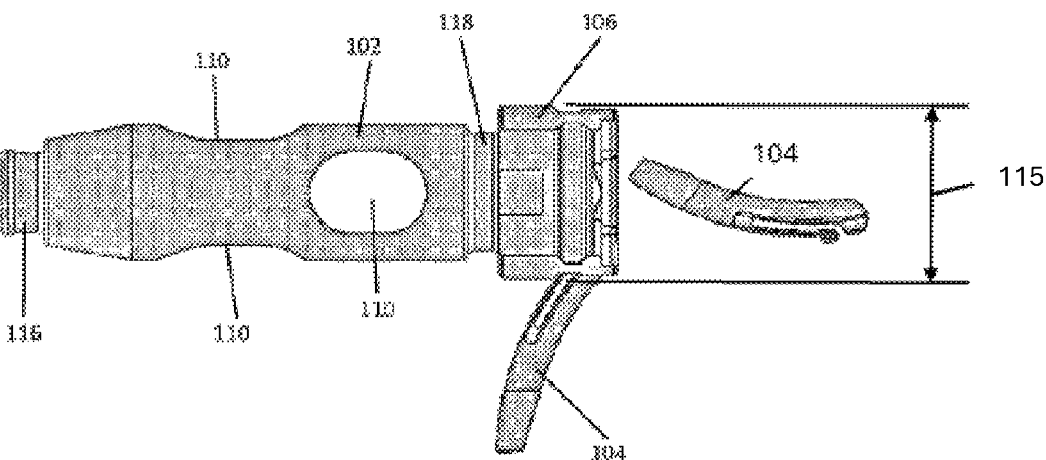
FIG. 2 is a top view of an implant anchor in accordance with certain embodiments of the present invention.
Figure 3:
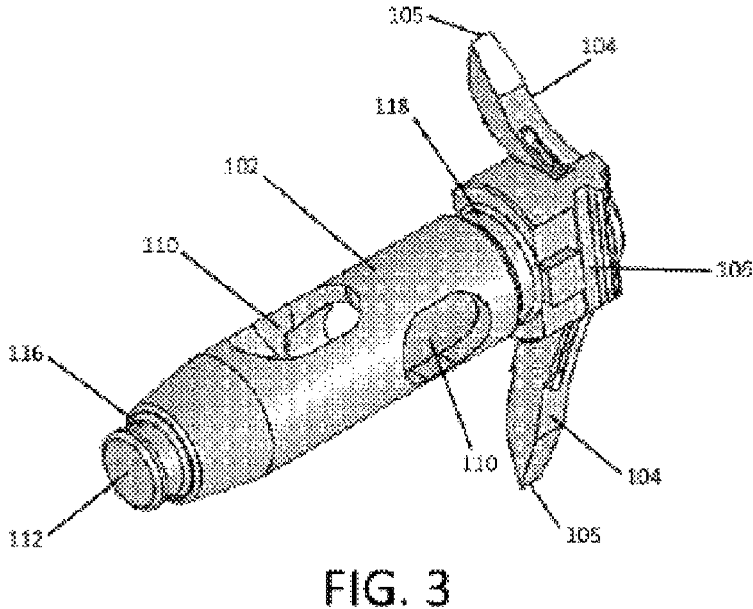
FIG. 3 is a perspective view of an implant anchor in accordance with certain embodiments of the present invention.

Referring to FIGS. 1-3, an anchor 100 is shown. The anchor 100 includes an elongated cylindrical body 102 and a pair of anchor arms 104 that are removably securable to a proximal head portion 106 of the body 102. The body 102 includes an aperture 108 defined at a proximal end thereof that continues distally at least partially though the body to define a hollow interior thereof. A plurality of lateral apertures 110 are provided through the body to allow fill material introduced through the proximal aperture 108 to exit the body through the lateral apertures 110 and thereby fill an implant attached or coupled to the anchor 100. The distal end 112 of the body 102 is enclosed, but can be open in alternative embodiments. The maximum diameter of the head portion 106 is shown in FIG. 2 using reference number 115.

Figure 4:
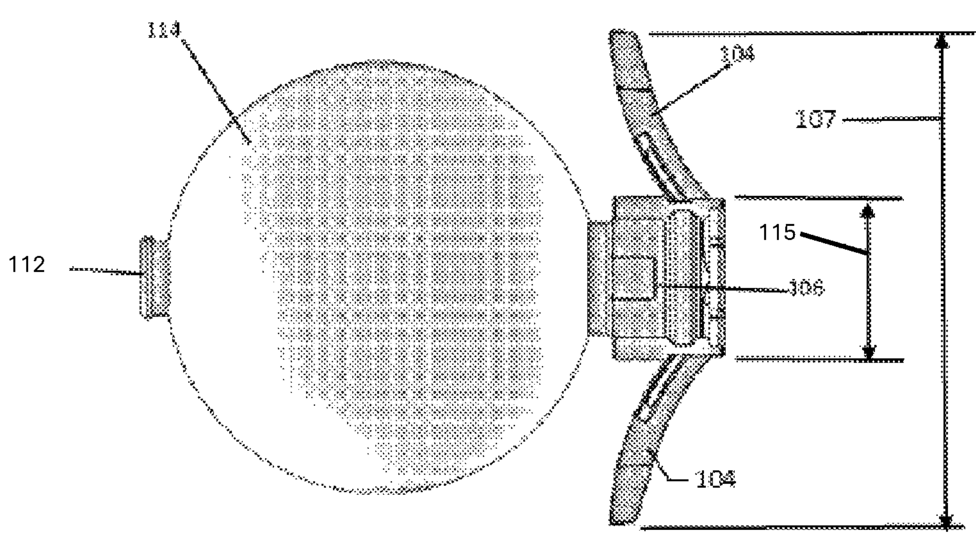
FIG. 4 is a top view of an implant anchor coupled to a spinal implant in accordance with certain embodiments of the present invention.

A first end of each of the anchor arms 104 are attached to the head portion 106 such that they generally face opposite directions from one another. Each anchor arm 104 is curved, but can be straight in alternative embodiments. The free or second end 105 of each anchor arm 104 is pointed such that the anchor arm can penetrate into a vertebral body to the anchor 100, and thereby the implant, from moving from its intended location and/or orientation. As can be seen in FIG. 4, the maximum lateral distance 107 of the anchor arms 104 is substantially greater than the maximum diameter 115 of the anchor head portion.

Figure 5:
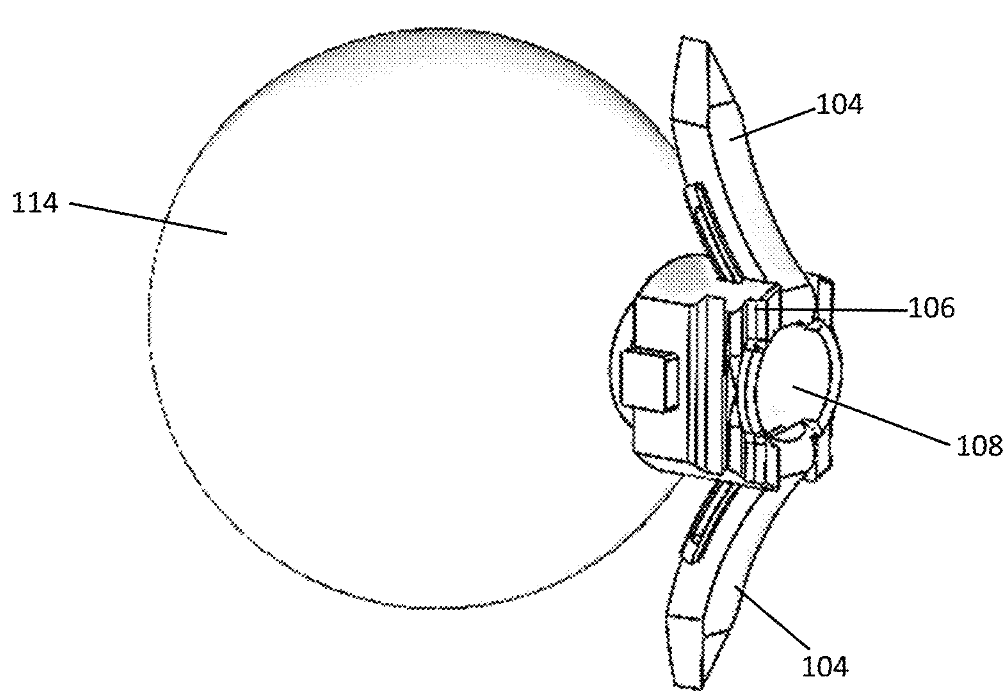
FIG. 5 is a perspective view of an implant anchor coupled to a spinal implant in accordance with certain embodiments of the present invention.

Referring additionally to FIGS. 4-5, an expandable implant 114 is secured to the body 102. The expandable implant 114 can be formed of expandable mesh. The expandable mesh can be porous. The implant 114 is secured circumferentially around a distal groove 116 defined at the distal end of the body 102 and circumferentially around a proximal groove 118 defined distally adjacent to the head portion 106. The implant 114, when joined to the body 102, defines an enclosed space that can be filled via the proximal aperture 108.

The implant 114 shown in FIGS. 4-5 is shown to be in an expanded or filled state. However, the implant is initially joined to the body as a combined surgical component or construct in its non-expanded state. The completed construct is only filled or expanded after its placement into the intervertebral or disc space as part of the spinal surgical procedure.

Figure 6:
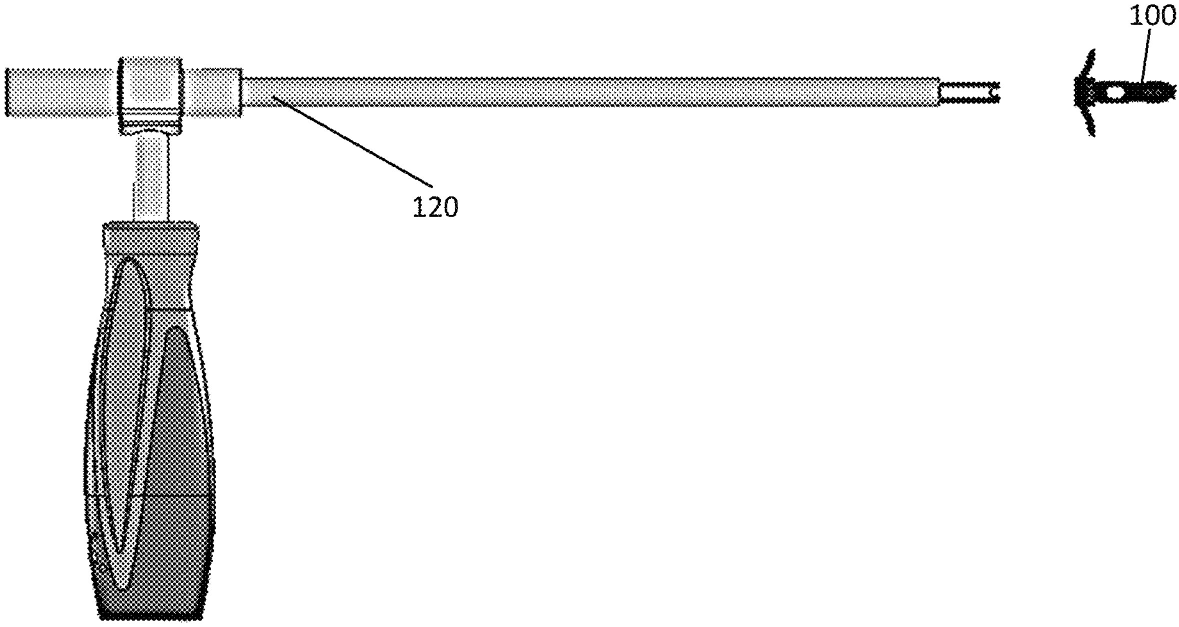
FIG. 6 is a side view of an insertion tool aligned with an implant anchor in accordance with certain embodiments of the present invention.
Figure 7:
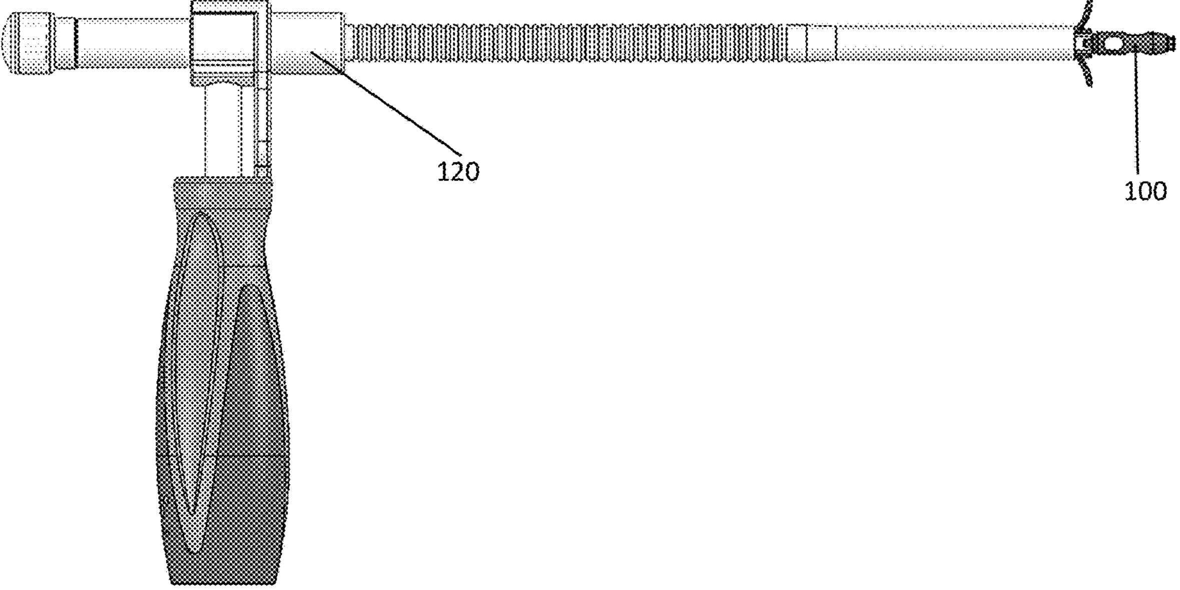
FIG. 7 is a side view of an implant anchor coupled to an insertion tool in accordance with certain embodiments of the present invention.

Referring to FIGS. 6 and 7, an inserter tool 120 is shown that is configured to releasably grasp the anchor 100 for an implantation procedure. Note that the expandable implant is not shown in FIGS. 6 and 7 to best illustrate the anchor body 102. However, the implant would already be combined with the anchor prior to coupling with the inserter tool 120.

The anchor arms 104 can be secured to the head portion 106 prior to implantation (wherein the maximum lateral dimension of the anchor 100 is the maximum diameter 115 of the anchor head portion) and expansion, or the arms 104 can be secured after the implant is expanded in situ. As can be seen from the FIGURES, when the anchor arms 104 are not secured to the head portion, the maximum lateral dimension of the anchor 100 is the maximum diameter 115 of the anchor head portion 106, and when the anchor arms 104 are secured to the head portion 106, the maximum lateral dimension of the anchor 100 is the maximum lateral distance 107 of the anchor arms 104. The arms 104 can also be removed from the head portion 106 to perform an explant procedure, if desired.

In use, the completed construct (anchor 100 with unexpanded implant 114 coupled thereto) is placed in the intervertebral space. The anchor arms 104 are aligned such that one arm penetrates into the superior vertebral body while the other arm penetrates into the inferior vertebral body. The arms 104 are secured to the head portion 106 either before or after the implant 114 is filled and/or expanded. The implant 114 can be expanded by filling it, for example, with bone graft in-situ to expand the mesh to create a large, endplate conforming, load-sharing graft pack that provides broad endplate contact, support and fusion.

The anchor 100, and in particular the arms 104, can be placed on and/or into the posterior aspect of the vertebral bodies.

In an example embodiment of the present invention, the surgical method may include the steps of:

1. Employing posterior access, including but not limited to in an embodiment through Kambin's triangle;
2. Removal of the intervertebral disc to expose the bony endplates for fusion and provide working space. This would be done all the way to the anterior aspect of the disc;
3. Sectioning of the ALL with the assistance of direct visualization, for example with an endoscope for safety;
4. Screw/rod placement to control lordosis;
5. Placement of the expandable implant/anchor construct in an unexpanded state;
6. Anchoring, fixation and or securing the implanted construct to the endplates and/or vertebral bodies. In an example embodiment the mesh may be placed anterior to the Instantaneous Axis of Rotation;
7. Filling/expansion if the implant to create lordotic intervertebral distraction;
8. Closure of the implant posteriorly; and
9. Placement of osteobiologic adjuvant posterior to the implant.

The ALL may be released anteriorly and the mesh implant may be placed from an anterior approach The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A method of anchoring an expandable mesh implant to a patient's anatomy, comprising:

providing an anchor having an elongated body, a first anchor arm, and a second anchor arm, wherein the elongated body extends lengthwise between a distal end and a proximal end, wherein the elongated body includes an interior aperture and a lateral aperture, and wherein the interior aperture extends lengthwise from the proximal end, and wherein the lateral aperture is disposed in the elongated body at a position between the distal end and the proximal end of the elongated body and the lateral aperture is in communication with the interior aperture;

wherein a first end of the first anchor arm is non-rotationally secured to the elongated body and a first end of the second anchor arm is non-rotationally secured to the elongated body;

securing the expandable mesh implant to the elongated body of the anchor while the expandable mesh implant is in an unexpanded state;

placing the expandable mesh implant secured to the elongated body in the unexpanded state in an intervertebral space located between a superior vertebrae and an inferior vertebrae;

securing the first anchor arm to the elongated body at the first end of the first anchor arm and extending an opposing second end of the first anchor arm at least partially into the superior vertebrae; and securing the second anchor arm to the elongated body at the first end of the second anchor arm and extending an opposing second end of the second anchor arm at least partially into the inferior vertebrae.

2. The method of claim 1, wherein the first end of the first anchor arm is secured to the elongated body adjacent to the proximal end of the elongated body, and the first end of the second anchor arm is secured to the elongated body adjacent to the proximal end of the elongated body.

3. The method of claim 1, wherein the second end of the first anchor arm is configured for non-rotational penetration into the superior vertebrae, and the second end of the second anchor arm is configured for non-rotational penetration into the inferior vertebrae.

4. The method of claim 1, wherein the first anchor arm and the second anchor arm are disposed on opposite sides of the elongated body.

5. The method of claim 1, wherein the elongated body includes a head portion contiguous with the proximal end, and the first end of the first anchor arm is secured to the head portion, and the first end of the second anchor arm is secured to the head portion.

6. The method of claim 1, wherein the first anchor arm has a curved configuration between the first end of the first anchor arm and the second end of the first anchor arm, and the second anchor arm has a curved configuration between the first end of the second anchor arm and the second end of the second anchor arm.

7. A method of anchoring an expandable mesh implant to a patient's anatomy, comprising:

providing an anchor having an elongated body, a first anchor arm, and a second anchor arm, wherein the elongated body extends lengthwise between a distal end and a proximal end, wherein the elongated body includes an interior aperture and a lateral aperture, and wherein the interior aperture extends lengthwise from the proximal end, and wherein the lateral aperture is disposed in the elongated body at a position between the distal end and the proximal end of the elongated body and the lateral aperture is in communication with the interior aperture;

removing the first anchor arm and the second anchor arm from the elongated body;

securing the expandable mesh implant to the elongated body of the anchor while the expandable mesh implant is in an unexpanded state;

placing the expandable mesh implant secured to the elongated body in the unexpanded state in an intervertebral space located between a superior vertebrae and an inferior vertebrae;

attaching the first anchor arm and the second anchor arm to the elongated body subsequent to placement of the expandable mesh implant secured to the elongated body in the unexpanded state in the intervertebral space located between the superior vertebrae and the inferior vertebrae;

securing the first anchor arm to the superior vertebrae and securing the second anchor arm to the inferior vertebrae; and filling the expandable mesh implant with a filler material.

8. The method of claim 7, wherein the first anchor arm (FAA) extends between a FAA first end and a FAA second end, and the FAA first end is secured to the elongated body adjacent to the proximal end of the elongated body; and wherein the second anchor arm (SAA) extends between a SAA first end and a SAA second end, and the SAA first end is secured to the elongated body adjacent to the proximal end of the elongated body.

9. The method of claim 8, wherein the FAA first end is non-rotationally secured to the elongated body and the SAA first end is non-rotationally secured to the elongated body.

10. The method of claim 9, wherein the FAA second end is configured for non-rotational penetration into the superior vertebrae, and the SAA second end is configured for non-rotational penetration into the inferior vertebrae.

11. The method of claim 8, wherein the first anchor arm has a curved configuration between the FAA first end and the FAA second end, and the second anchor arm has a curved configuration between the SAA first end and the SAA second end.

12. The method of claim 7, wherein the first anchor arm and the second anchor arm are disposed on opposite sides of the elongated body.

13. The method of claim 7, wherein the elongated body includes a head portion contiguous with the proximal end, and the first anchor arm is secured to the head portion, and the second anchor arm is secured to the head portion.

14. A method of anchoring an expandable mesh implant to a patient's anatomy, comprising:

providing an anchor having an elongated body, a first anchor arm, and a second anchor arm, wherein the elongated body extends lengthwise between a distal end and a proximal end, wherein the elongated body includes an interior aperture and a lateral aperture, and wherein the interior aperture extends lengthwise from the proximal end, and wherein the lateral aperture is disposed in the elongated body at a position between the distal end and the proximal end of the elongated body and the lateral aperture is in communication with the interior aperture;

removing the first anchor arm and the second anchor arm from the elongated body;

securing the expandable mesh implant to the elongated body of the anchor while the expandable mesh implant is in an unexpanded state;

placing the expandable mesh implant secured to the elongated body in the unexpanded state in an intervertebral space located between a superior vertebrae and an inferior vertebrae;

attaching the first anchor arm and the second anchor arm to the elongated body;

securing the first anchor arm to the superior vertebrae and securing the second anchor arm to the inferior vertebrae; and filling the expandable mesh implant with a filler material;

wherein the elongated body includes a head portion contiguous with the proximal end, and the first anchor arm is secured to the head portion, and the second anchor arm is secured to the head portion; and wherein the first anchor arm is non-rotationally secured to the head portion and the second anchor arm is non-rotationally secured to the head portion.

* * * * *